(12) United States Patent
Pollak et al.

(10) Patent No.: US 10,093,957 B2
(45) Date of Patent: *Oct. 9, 2018

(54) METHOD, KIT AND SYSTEM FOR IMAGING A BLOOD SAMPLE

(71) Applicant: S.D. SIGHT DIAGNOSTICS LTD., Jerusalem (IL)

(72) Inventors: Joseph Joel Pollak, Neve Daniel (IL); Arnon Houri Yafin, Jerusalem (IL); Seth J. Salpeter, Jerusalem (IL)

(73) Assignee: S.D. SIGHT DIAGNOSTICS LTD., Tel Aviv (IL)

( * ) Notice: Subject to any disclaimer, the term of this patent is extended or adjusted under 35 U.S.C. 154(b) by 226 days.

This patent is subject to a terminal disclaimer.

(21) Appl. No.: 15/083,610

(22) Filed: Mar. 29, 2016

(65) Prior Publication Data

US 2016/0208306 A1    Jul. 21, 2016

Related U.S. Application Data

(63) Continuation of application No. 14/440,864, filed as application No. PCT/IL2014/050585 on Jun. 30, 2014, now Pat. No. 9,329,129.

(30) Foreign Application Priority Data

Jul. 1, 2013    (IL) .......................................... 227276

(51) Int. Cl.
*C12Q 1/04*    (2006.01)
*G01N 21/64*    (2006.01)
(Continued)

(52) U.S. Cl.
CPC ............. *C12Q 1/04* (2013.01); *G01N 1/2813* (2013.01); *G01N 1/38* (2013.01); *G01N 15/1463* (2013.01);
(Continued)

(58) Field of Classification Search
CPC .......... C12Q 1/04; G01N 1/2813; G01N 1/38; G01N 15/1463; G01N 15/1475;
(Continued)

(56) References Cited

U.S. PATENT DOCUMENTS 3,603,156 A    9/1971 Konkol
3,676,076 A    7/1972 Grady
(Continued)

FOREIGN PATENT DOCUMENTS

CN    101403650 A    4/2009
CN    102387864 A    3/2012
(Continued)

OTHER PUBLICATIONS

An International Search Report and a Written Opinion both dated Sep. 24, 2014, which issued during the prosecution of Applicant's PCT/IL2014/050423.
(Continued)

*Primary Examiner* — Edward Park
(74) *Attorney, Agent, or Firm* — Vorys, Sater, Seymour and Pease LLP

(57) ABSTRACT

Provided is a method for imaging a blood sample and a kit and system for executing the method. The method includes introducing a cell suspension including red blood cells onto a base surface of a carrier having a vertical height (H) being greater than or equal to a vertical depth (h) of the cell suspension when on the base carrier, the cell suspension including a cell concentration (C) being determined by a defined function; allowing the cells in the cell suspension to settle on the base surface of the carrier to form a monolayer of cells thereon; and acquiring at least one microscope image of at least a portion of the monolayer of cells; wherein the at least one microscope image is obtained by a microscope set to Depth Of Field that is not more than 20% of the
(Continued)

vertical height of the cell suspension settled on the base surface.

22 Claims, 6 Drawing Sheets

(51) Int. Cl.
| | |
|---|---|
| *G02B 21/36* | (2006.01) |
| *G01N 33/49* | (2006.01) |
| *G01N 1/28* | (2006.01) |
| *G01N 1/38* | (2006.01) |
| *G01N 15/14* | (2006.01) |
| *G01N 15/00* | (2006.01) |

(52) U.S. Cl.
CPC ..... *G01N 15/1475* (2013.01); *G01N 21/6428* (2013.01); *G01N 21/6486* (2013.01); *G01N 33/49* (2013.01); *G02B 21/361* (2013.01); *G01N 2015/0065* (2013.01); *G01N 2021/6439* (2013.01)

(58) Field of Classification Search
CPC .......... G01N 21/6428; G01N 21/6486; G01N 33/49; G01N 2015/0065; G01N 2021/6439; G02B 21/361
See application file for complete search history.

(56) References Cited

U.S. PATENT DOCUMENTS

| | | | |
|---|---|---|---|
| 3,967,056 A | 6/1976 | Yata et al. | |
| 4,076,419 A | 2/1978 | Kleker | |
| 4,209,548 A | 6/1980 | Bacus | |
| 4,350,884 A | 9/1982 | Dieter | |
| 4,454,235 A | 6/1984 | Johnson | |
| 4,494,479 A | 1/1985 | Drury et al. | |
| 4,700,298 A | 10/1987 | Palcic et al. | |
| 4,761,381 A | 8/1988 | Blatt et al. | |
| 4,774,192 A | 9/1988 | Terminiello et al. | |
| 4,803,352 A | 2/1989 | Bierleutgeb | |
| 4,849,340 A | 7/1989 | Oberhardt | |
| 4,902,101 A | 2/1990 | Fujihara et al. | |
| 5,001,067 A | 3/1991 | Coleman et al. | |
| 5,064,282 A | 11/1991 | Curtis | |
| 5,229,265 A | 7/1993 | Tometsko | |
| 5,300,779 A | 4/1994 | Hillman et al. | |
| 5,430,542 A | 7/1995 | Shepherd et al. | |
| 5,672,861 A | 9/1997 | Fairley et al. | |
| 5,674,457 A | 10/1997 | Williamsson et al. | |
| 5,745,804 A | 4/1998 | Iwane | |
| 5,782,770 A | 7/1998 | Mooradian et al. | |
| 5,932,872 A | 8/1999 | Price | |
| 5,948,686 A | 9/1999 | Wardlaw | |
| 5,985,595 A | 11/1999 | Krider et al. | |
| 6,074,879 A | 6/2000 | Zelmanovic et al. | |
| 6,101,404 A | 8/2000 | Yoon et al. | |
| 6,262,798 B1 | 7/2001 | Shepherd et al. | |
| 6,320,979 B1 | 11/2001 | Melen | |
| 6,350,613 B1 | 2/2002 | Wardlaw et al. | |
| 6,448,024 B1 | 9/2002 | Bruegger | |
| 6,632,681 B1 | 10/2003 | Chu | |
| 6,819,408 B1 | 11/2004 | Scrivens et al. | |
| 6,831,733 B2 | 12/2004 | Pettersson et al. | |
| 6,834,237 B2 | 12/2004 | Noergaard et al. | |
| 7,034,883 B1 | 4/2006 | Rosenqvist | |
| 7,329,537 B2 | 2/2008 | Qiu | |
| 7,344,890 B2 | 3/2008 | Perez et al. | |
| 7,417,213 B2 | 8/2008 | Krief et al. | |
| 7,706,862 B2 | 4/2010 | Alfano et al. | |
| 7,713,474 B2 | 5/2010 | Schulman et al. | |
| 7,998,435 B2 | 8/2011 | Reed | |
| 8,105,554 B2 | 1/2012 | Kanigan et al. | |
| D655,421 S | 3/2012 | Lee et al. | |
| 8,216,832 B2 | 7/2012 | Battrell et al. | |
| 8,345,227 B2 | 1/2013 | Zahniser et al. | |
| 8,477,294 B2 | 7/2013 | Zahniser et al. | |
| 8,481,303 B2 | 7/2013 | Faris et al. | |
| 8,488,111 B2 | 7/2013 | Zahniser et al. | |
| 8,491,499 B2 | 7/2013 | Choi et al. | |
| 8,922,761 B2 | 12/2014 | Zahniser et al. | |
| 9,012,868 B2 | 4/2015 | Courtney et al. | |
| 9,050,595 B2 | 6/2015 | Miller et al. | |
| 9,186,843 B2 | 11/2015 | Chan et al. | |
| 9,240,043 B2 | 1/2016 | Christiansen et al. | |
| 9,329,129 B2* | 5/2016 | Pollak | G01N 15/1463 |
| 2002/0009711 A1* | 1/2002 | Wada | C12Q 1/6841 435/4 |
| 2002/0028158 A1 | 3/2002 | Wardlaw | |
| 2003/0017085 A1 | 1/2003 | Kercso et al. | |
| 2003/0161514 A1 | 8/2003 | Curry | |
| 2003/0227612 A1 | 12/2003 | Fein et al. | |
| 2004/0132171 A1 | 7/2004 | Rule et al. | |
| 2004/0185447 A1 | 9/2004 | Maples et al. | |
| 2004/0218804 A1* | 11/2004 | Affleck | C30B 7/00 382/141 |
| 2004/0241677 A1 | 12/2004 | Lin et al. | |
| 2006/0063185 A1 | 3/2006 | Vannier | |
| 2006/0187442 A1 | 8/2006 | Chang et al. | |
| 2006/0223052 A1* | 10/2006 | MacDonald | C12Q 1/04 435/5 |
| 2006/0223165 A1 | 10/2006 | Chang et al. | |
| 2007/0054350 A1 | 3/2007 | Walker | |
| 2007/0252984 A1 | 11/2007 | Van Beek et al. | |
| 2008/0187466 A1 | 8/2008 | Wardlaw | |
| 2008/0212069 A1 | 9/2008 | Goldberg et al. | |
| 2008/0273776 A1 | 11/2008 | Krief et al. | |
| 2008/0305514 A1* | 12/2008 | Alford | C12Q 1/04 435/34 |
| 2009/0066934 A1* | 3/2009 | Gao | G01N 15/1463 356/73 |
| 2009/0075324 A1 | 3/2009 | Pettersson | |
| 2009/0185734 A1 | 7/2009 | Lindberg et al. | |
| 2009/0191098 A1 | 7/2009 | Beard et al. | |
| 2009/0269799 A1* | 10/2009 | Winkelman | G01N 1/2813 435/29 |
| 2010/0112631 A1 | 5/2010 | Hur et al. | |
| 2010/0120129 A1 | 5/2010 | Amshey et al. | |
| 2010/0157086 A1 | 6/2010 | Segale et al. | |
| 2010/0256918 A1* | 10/2010 | Chen | C12Q 1/6869 702/19 |
| 2010/0265323 A1 | 10/2010 | Perz | |
| 2011/0030458 A1 | 2/2011 | Park et al. | |
| 2011/0123398 A1 | 5/2011 | Carrilho et al. | |
| 2011/0149097 A1 | 6/2011 | Danuser et al. | |
| 2011/0151502 A1 | 6/2011 | Kendall et al. | |
| 2011/0178716 A1* | 7/2011 | Krockenberger | G01N 15/147 702/19 |
| 2011/0275111 A1 | 11/2011 | Pettigrew et al. | |
| 2012/0021951 A1 | 1/2012 | Hess et al. | |
| 2012/0030618 A1 | 2/2012 | Leong et al. | |
| 2012/0058504 A1 | 3/2012 | Li et al. | |
| 2012/0092477 A1 | 4/2012 | Kawano et al. | |
| 2012/0120221 A1* | 5/2012 | Dong | G01N 15/1434 348/77 |
| 2012/0169863 A1 | 7/2012 | Bachelet et al. | |
| 2012/0225446 A1* | 9/2012 | Wimberger-Friedl | B01L 3/5025 435/29 |
| 2012/0320045 A1 | 12/2012 | Yao et al. | |
| 2013/0023007 A1 | 1/2013 | Zahniser et al. | |
| 2013/0130262 A1* | 5/2013 | Battrell | B01L 3/50273 435/6.12 |
| 2013/0176551 A1 | 7/2013 | Wardlaw et al. | |
| 2014/0139625 A1 | 5/2014 | Mathuis et al. | |
| 2014/0139630 A1* | 5/2014 | Kowalevicz | G03B 17/00 348/46 |
| 2014/0205176 A1 | 7/2014 | Obrien et al. | |
| 2014/0347459 A1 | 11/2014 | Greenfield et al. | |
| 2015/0037806 A1 | 2/2015 | Pollak et al. | |
| 2015/0278575 A1* | 10/2015 | Allano | G06K 9/00127 382/133 |

(56) References Cited

U.S. PATENT DOCUMENTS

| | | | | |
|---|---|---|---|---|
| 2015/0302237 | A1* | 10/2015 | Ohya | G06K 9/00147 |
| | | | | 382/133 |
| 2015/0316477 | A1* | 11/2015 | Pollak | G01N 15/1463 |
| | | | | 435/40.51 |
| 2016/0246046 | A1 | 8/2016 | Yorav Raphael et al. | |
| 2017/0052110 | A1 | 2/2017 | Malissek et al. | |
| 2017/0160185 | A1 | 6/2017 | Minemura et al. | |

FOREIGN PATENT DOCUMENTS

| | | | |
|---|---|---|---|
| EP | 0073551 | A2 | 3/1983 |
| EP | 0 479 231 | A1 | 4/1992 |
| EP | 1 698 883 | A1 | 9/2006 |
| EP | 2145684 | A2 | 1/2010 |
| EP | 3 001 174 | A1 | 3/2016 |
| JP | 61-198204 | A | 9/1986 |
| JP | 11-73903 | A | 3/1999 |
| JP | 2000-199845 | A | 7/2000 |
| JP | 2004-257768 | A | 9/2004 |
| JP | 2006-301270 | A | 11/2006 |
| JP | 2007040814 | A | 2/2007 |
| WO | 96/01438 | A1 | 1/1996 |
| WO | 96/12981 | A1 | 5/1996 |
| WO | 00/55572 | A1 | 9/2000 |
| WO | 03/056327 | A1 | 7/2003 |
| WO | 03/073365 | A1 | 9/2003 |
| WO | 2004/111610 | A2 | 12/2004 |
| WO | 2005/121863 | A1 | 12/2005 |
| WO | 2006/121266 | A1 | 11/2006 |
| WO | 2008/063135 | A1 | 5/2008 |
| WO | 2010/056740 | A1 | 5/2010 |
| WO | 2010/126903 | A1 | 11/2010 |
| WO | 2011/143075 | A2 | 11/2011 |
| WO | 2012/000102 | A1 | 1/2012 |
| WO | 2012/030313 | A1 | 3/2012 |
| WO | 2012/090198 | A2 | 7/2012 |
| WO | 2012/154333 | A1 | 11/2012 |
| WO | 2013/098821 | A1 | 7/2013 |
| WO | 2014/159620 | A1 | 10/2014 |
| WO | 2014/188405 | A1 | 11/2014 |
| WO | 2015/001553 | A1 | 1/2015 |
| WO | 2015/029032 | A1 | 3/2015 |
| WO | 2016/030897 | A1 | 3/2016 |
| WO | 2017/046799 | A1 | 3/2017 |

OTHER PUBLICATIONS

Guy et al. "The use of fluorescence enhancement to improve the microscopic diagnosis of falciparum malaria" Malaria Journal 2007, 6:89 http://www.malariajournal.com/content/6/1/89 (Jul. 6, 2007).

Eriksson et al: "Automated focusing of nuclei for time lapse experiments on single cells using holographic optical tweezers", Optics Express, vol. 17, No. 7, Mar. 24, 2009, pp. 5585-5594.

An International Search Report and a Written Opinion both dated Jan. 15, 2016, which issued during the prosecution of Applicant's PCT/IL2015/050864.

An International Search Report and a Written Opinion both dated Apr. 18, 2013, which issued during the prosecution of Applicant's PCT/IL2012/050556.

Cervantes et al. "High-content live cell imaging with RNA probes: advancements in high-throughput antimalarial drug discovery" BMC Cell Biology 2009, 10:45 www.biomedcentral.com/1471-2121/10/45 (Jun. 10, 2009).

Xu et al. "Plasmodium yoelii: A differential fluorescent technique using Acridine Orange to identify infected erythrocytes and reticulocytes in Duffy knockout mouse" Experimental Parasitology vol. 110, Issue 1, May 2005, pp. 80-87. http://www.sciencedirect.com/science/article/ pii/S001448940500038X : (May 31, 2005).

Office Action dated Oct. 5, 2016, which issued during the prosecution of U.S. Appl. No. 14/285,672.

Groen et al: "A Comparison of Different Focus Functions for Use in Autofocus Algorithms", Cytometry, Alan Liss, New York, US, vol. 6, No. 2, Mar. 1, 1985 (Mar. 1, 1985), pp. 81-91.

Gordon et al: "Supplementary Note to Gordon et al: "Single-cell quantification of molecules . . . "", Nature Methods, Jan. 21, 2007, pp. 1-35.

Gordon et al: "Single-cell quantification of molecules and rates using open-source microscope-based cytometry", HHS Public Access Author Manuscript, vol. 4, No. 2, Jan. 21, 2007, pp. 175-181.

European Search Report dated Dec. 14, 2016, which issued during the prosecution of Applicant's European App No. 14800352.8.

Yazdanfar et al., 2008. Simple and robust image-based autofocusing for digital microscopy. Optics express, 16(12), pp. 8670-8677.

Bravo-Zanoguera et al., 2007. Dynamic autofocus for continuous-scanning time-delay-and-integration image acquisition in automated microscopy. Journal of biomedical optics, 12(3), pp. 034011-034011.

Agero et al., 2004. Defocusing microscopy. Microscopy research and technique, 65(3), pp. 159-165.

Bacus, 1985. Cytometric approaches to red blood cells. Pure and Applied Chemistry, 57(4), pp. 593-598.

Roma et al. "Total three-dimensional imaging of phase objects using defocusing microscopy: Application to red blood cells." Applied Physics Letters 104.25 (2014): 251107.

An Office Action dated Mar. 2, 2017, which issued during the prosecution of U.S. Appl. No. 14/369,251.

An International Search Report and a Written Opinion both dated Jan. 23, 2017, which issued during the prosecution of Applicant's PCT/IL2016/051025.

An International Preliminary Report on Patentability dated Feb. 28, 2017, which issued during the prosecution of Applicant's PCT/IL2015/050864.

European Search Report dated Mar. 23, 2017, which issued during the prosecution of Applicant's European App No. 14839661.7.

Keiser et al., "Acridine Orange for malaria diagnosis: its diagnostic performance, its promotion and implementation in Tanzania, and the implications for malaria control", Annals of Tropical Medicine & Parasitology, vol. 96, No. 7, pp. 643-654, (2002).

Anand et al., "Automatic Identification of Malaria-Infected RBC With Digital Holographic Microscopy Using Correlation Algorithms", vol. 4, No. 5, pp. 1456-1464, (2012).

CDC Centers for Disease Control and Prevention, "DPDx—Laboratory Identification of Parasitic Diseases of Public Health Concern", CDC—DPDx—Diagnostic Procedures—Blood Specimens—Microscopic Examination, three pages, found online at http://www.cdc.gov/dpdx/diagnosticProcedures/blood/microexam.html, (2014).

Chong et al., "Line-scan focal modulation microscopy for rapid imaging of thick biological specimens", SPIE/OSA/IEEE Asia Communications and Photonics, International Society for Optics and Photonics, five pages, (2011).

Life Technologies Corporation, "Counting blood cells with Countless Automated Cell Counter" found at http://www.lifetechnologies.com/content/dam/LifeTech/migration/files/cell-tissue-analysis/pdfs.par.83996.file.dat/w-082149-countless-application-blood-cells.pdf, four pages, (2009).

Frean, "Microscopic determination of malaria parasite load: role of image analysis", Microscopy: Science, Technology, Applications and Education, pp. 862-866, (2010).

Kawamoto, "Rapid diagnosis of malaria by fluorescence microscopy with light microscope and interference filter", Lancet, vol. 337, pp. 200-202, (1991).

Kawamoto, et al., "Rapid diagnosis of malaria by fluorescence microscopy", Parasitology Today, vol. 8, No. 2, pp. 69-71, (1992).

Knesel, "Roche Image Analysis Systems, Inc.", Acta Cytologica, vol. 40, pp. 60-66, (1996).

Leif, "Methods for Preparing Sorted Cells as Monolayer Specimens", Springer Lab Manuals, Section 7—Chapter 5, pp. 592-619, (2000).

Merchant et al., "Computer-Assisted Microscopy", The essential guide to image processing, Chapter 27, pp. 777-831, Academic Press, (2009).

Moody, "Rapid Diagnostic Tests for Malaria Parasites", Clinical Microbiology Reviews, vol. 15, No. 1, pp. 66-78, (2002).

Ortyn et al., "Extended Depth of Field Imaging for High Speed Cell Analysis", Cytometry Part A, vol. 71A, pp. 215-231, (2007).

(56) References Cited

OTHER PUBLICATIONS

Osibote et al., "Automated focusing in bright-field microscopy for tuberculosis detection", J Microsc., vol. 240, No. 2, pp. 155-163, (2010).
Price et al., "Comparison of Phase-Contrast and Fluorescence Digital Autofocus for Scanning Microscopy", Cytometry, vol. 16, pp. 283-297, (1994).
Purwar et al., "Automated and unsupervised detection of malarial parasites in microscopic images", Malaria Journal, vol. 10, No. 1, p. 364 (pp. 1-10), (2011).
Shen et al., "Digital Autofocus Methods for Automated Microscopy", Methods in Enzymology, vol. 414, pp. 620-632, (2006).
Shute et al., "Identification of malaria parasites by fluorescence microscopy and acridine orange staining", Bulletin of the World Health Organization, vol. 48, No. 5, pp. 591-596, (1973).
Sun et al., "Autofocusing Algorithm Selection in Computer Microscopy", Intelligent Robots and Systems, 2005 IEEE/RSJ International Conference on Intelligent Robots and Systems, pp. 419-425, (2005).
Tek et al., "Computer vision for microscopy diagnosis of malaria", Malaria Journal, vol. 8, p. 153 (pp. 1-14), (2009).
Thung et al., "Blood Parasite Identification using Feature Based Recognition", International Conference on Electrical Engineering and Informatics (ICEEI), pp. 1-4, (2011).
Vink et al., "An automatic vision-based malaria diagnosis system", Journal of Microscopy, vol. 250, No. 3, pp. 166-178, (2013).
Wu, "Autofocusing", Microscope Image Processing, Chapter 16, pp. 441-467, Academic Press, (2010).
Yang et al., "A Rapid Auto-focus Method in Automatic Microscope", 9th International Conference on Signal Processing, ICSP 2008, pp. 502-505, (2008).
Zahniser et al., Automated Slide Preparation System for the Clinical Laboratory, Cytometry, vol. 26, No. 10, pp. 50-64, (1996).
Matcher et al., "Use of the water absorption spectrum to quantify tissue chromophore concentration changes in near-infrared spectroscopy." Phys. Med. Biol., vol. 38, pp. 177-196, (1994).
Rappaz et al., "Comparative study of human erythrocytes by digital holographic microscopy, confocal microscopy, and impedance volume analyzer." Cytometry Part A, vol. 73A, pp. 895-903, (2008).
Ross et al., "Automated image processing method for the diagnosis and classification of malaria on thin blood smears." Med and Biol Eng Comput, vol. 44, pp. 427-436, (2006).
Vink et al., "An automatic vision-based malaria diagnosis system." Journal of microscopy, vol. 250, Issue 3, pp. 166-178, (2013).
Houri-Yafin et al., "An enhanced computer vision platform for clinical diagnosis of malaria." Malaria Contr Eliminination, vol. 5, Issue 1, 1000138, 5 pages, (2016).
Ahirwar et al., "Advanced image analysis based system for automatic detection and classification of malarial parasite in blood images." International Journal of Information Technology and Knowledge Management, vol. 5, No. 1, pp. 59-64, (2012).
An Office Action dated Aug. 4, 2017, which issued during the prosecution of U.S. Appl. No. 14/369,251.
Office Action dated Jun. 13, 2017, which issued during the prosecution of U.S. Appl. No. 14/285,672.
Office Action dated Jul. 11, 2017, which issued during the prosecution of U.S. Appl. No. 15/174,672.

* cited by examiner

METHOD, KIT AND SYSTEM FOR IMAGING A BLOOD SAMPLE

CROSS-REFERENCES TO RELATED APPLICATIONS

The present application is a continuation of U.S. Ser. No. 14/440,864 to Pollak (published as US 2015/0316477), which is the US national phase application of PCT Application No. PCT/IL/2014/050585 to Pollak (published as WO 15/001553), filed Jun. 30, 2014, which claims priority from Israel Patent Application No. 227276, filed Jul. 01, 2013.

TECHNOLOGICAL FIELD

The present disclosure is in the field of microbiology and in particular to methods relating to cell sample preparations and imaging thereof, for use, inter alia, in diagnosis.

PRIOR ART

References considered to be relevant as background to the presently disclosed subject matter are listed below:
- Anthony Moody *Various rapid diagnostic tests for Malaria parasite* in Clinical Microbiology Reviews January 2002 p. 66-78;
- Vink J P. et al. *An automatic vision-based malaria diagnosis system Journal of Microscopy,* 2013, p. 1-13;
- International patent application publication No. WO 2010/116341;
- "*Counting blood cells with countess Automated Cell Counter*" found at http://www.lifetechnologies.com/content/dam/LifeTech/migraction/files/cell-tissue-analysis/pdfs.par83996.file.dat/w-082149-countess-application-blood-cells.pdf;
- U.S. Pat. No. 4,209,548;
- U.S. Pat. No. 4,494,479;
- U.S. Pat. No. 6,819,408;
- Leif R C. et al *Methods for Preparing Sorted Cells as Monolayer Specimens,* Springer Lab Manuals 2000 p. 592-619;
- Zahniser D J et al. *Automated Slide Preparation System for the Clinical Laboratory,* Cytometry 1996 Mar. 15; 26(10):60-4;
- Knessel E A et al. *Roche Image Analysis Systems, Inc.* Acta Cytologica 1996; 40:60-66;

Acknowledgement of the above references herein is not to be inferred as meaning that these are in any way relevant to the patentability of the presently disclosed subject matter.

BACKGROUND

Cell slides are ordinarily prepared during a cytopathology procedure, i.e. studying and diagnosing diseases on the cellular level. One of the most prevalent methods of slide preparation is smearing. The samples are smeared across a glass microscope slide for subsequent staining and microscopic examination. The smearing method is required in order to acquire a thin layer of cells on the slide, thus enabling focusing on and imaging the cells. However, smearing might cause a change in cell morphology. In addition, with smearing it is difficult to accurately and stably image living cells, for at least the reason that cells dry out quickly and additional staining without fixation is almost impossible.

Anthony Moody describes [*Various rapid diagnostic tests for Malaria parasite* in Clinical Microbiology Reviews January 2002 p. 66-78] inter alia, preparation of thin blood films containing a monolayer of red blood cells and multi-layered thick blood films.

Reference to Moody is later made by Vink J P. et al. [*An automatic vision-based malaria diagnosis system* Journal of Microscopy, 2013, p. 1-13] which describes a quantitative cartridge-scanner system for vision-based malaria diagnosis, focusing on low malaria parasite densities. The proposed cartridge allows the formation of a thin blood film and detection of *Plasmodium falciparum*. To be able to determine the parasite density, Vink et al. aimed at forming a thin blood film containing a monolayer of red blood cell and based their design on the cartridge described in International patent application publication No. WO 2010/116341 (US patent application publication No. 20120225446).

Specifically, WO 2010/116341 describes an apparatus for producing thin layers of a fluid sample for analysis, that has a two dimensional array of analysis chambers, and a branching pattern of entry channels coupled to the array to enable the analysis chambers to be filled in parallel. The analysis chambers are planar with a height less than that of the entry channels so as to produce the thin layers when filled with the fluid sample. The analysis chambers can be suitable for capillary filling by a specified fluid sample such as blood. The analysis chambers should not be more than 15 μm high in order for the cells to form a monolayer. Manufacturing of chambers having height of this order is not always possible and is relatively expensive. U.S. Pat. No. 4,209,548 describes a method wherein a blood sample on a slide is spun to create a monolayer of randomly distributed red blood cells. To inhibit cell morphology distortion from occurring during drying, the morphologies of the cells contained in the monolayer are preserved by a fixing agent after monolayer preparation but prior to drying. U.S. Pat. No. 4,494,479 describes a device for preparing a monolayer film of a biological fluid sample on a slide device that includes a base for retaining a slide thereon and a spreader manually movable linearly relative to the base and slide in a pass which spreads a sample of the fluid on the slide into such a monolayer.

The publication "*Counting blood cells with countess Automated Cell Counter*" describes preparation of blood samples for counting white/red blood cells that involves dilution of the blood cells.

U.S. Pat. No. 6,819,408 describes a method and apparatus for analyzing a blood or another biological fluid sample in a quiescent state without the need for additional diluting reagents or fluid streams passing through the apparatus during the analytic process. The method and apparatus allow enumeration of particulate constituents of biological samples and inspection thereof using an optical scanning instrument.

Leif R C et al (Methods for Preparing Sorted Cells as Monolayer Specimens) Springer Lab Manuals 2000 describes the application of a method of centrifugal cytology for creating a monolayer from cells that were previously sorted using a cell sorter (FACS). According to Lief, Centrifugal Cytology is the process where cells in suspension are centrifuged onto a substrate and then fixed concurrently with the application of centrifugal force.

Knessel E A et al (Roche Image Analysis Systems) Acta Cytologica 1996 describes the application of ma a batch centrifugation process together with a computer controlled robotic pipetting station to prepared a monolayer from a suspension of cervical sample.

Zahniser D J et al. (Automated Slide Preparation System for Clinical Laboratory) Cytometry 1996, describes an automated device that collects cells from suspension and disperses them as a monolayer on a glass slide using filter-transfer technology.

GENERAL DESCRIPTION

The present disclosure provides a method for imaging a blood sample, the method comprising:
- introducing a cell suspension comprising red blood cells, onto a base surface of a carrier having a vertical height (H) being greater than or equal to a vertical depth (h) of said cell suspension when on said base carrier, the cell suspension comprising a cell concentration (C) being determined by the function:

$C=F/(h*pi/4*d^2)$ (F) being a desired base surface coverage; and (d) being an average cell dimension of the cells in the cell suspension;
- allowing the cells in the cell suspension to settle on said base surface of the carrier to form on the base surface of the carrier a monolayer of cells;
- acquiring at least one microscope image of at least a portion of the monolayer of cells,
- wherein said at least one microscope image is obtained by a microscope set to Depth Of Field (DOF) that is not more than 20% of the vertical height of the cell suspension when settled on said base surface.

Also provided by the present disclosure, a kit for imaging a blood sample, the kit comprising:
- a carrier comprising a base surface and a vertical height (H); and
- instructions for performing the steps of:
  - providing a cell suspension from a blood sample comprising red blood cells, the cell suspension being of a cell concentration (C) determined by the function:

$C=F/(h*pi/4*d^2)$ (F) being a desired base surface coverage; and (d) being an average cell dimension of the cells in the cell suspension;
  - introducing the cell suspension of the desired concentration C onto the base surface of the carrier, the cell suspension having said vertical depth (h) when in said carrier, said vertical depth (h) being smaller or equal to the vertical height (H);
  - allowing the cells in the cell suspension to settle on said base surface of the carrier to form onto the base surface a monolayer of cells;
  - acquiring at least one microscope image of at least a portion of the monolayer of cells,
    - wherein said at least one microscope image is obtained by setting the microscope to a Depth Of Field (DOF) that is not more than 20% of the vertical height of the cell suspension when settled on said base surface.

Yet further, there is provided by the present disclosure a system for imaging a blood sample comprising:
- one or more reservoir units for holding, respectively, one or more sample treatment agents comprising at least one blood cells diluting agent;
- a blood sample preparing unit being in fluid communication with said one or more reservoir units and configured to receive a blood sample comprising red blood cells and amount of at least one blood cell diluting agent and to form therefrom a blood cells suspension, the amount of said at least one cell diluting agent being determined so as to dilute said sample of cells by a dilution factor (D) so as to provide a cell concentration (C);
- a microscope image acquisition unit for acquiring at least one image of the blood cells suspension when on a base surface of a carrier, the carrier having a vertical height (H) being greater or equal to a vertical depth (h) of said cell suspension when on said base surface;
- a control unit being configured to:
  - provide dilution factor D of diluting said sample, factor D being a function of the desired base surface coverage (F), the average cell dimension d of cell blood cells, and the vertical depth h of said suspension of cells that provides a monolayer of the cells when settled on said base surface of the carrier; and
  - acquire at least one microscope image of the cell suspension by a microscope set to a Depth Of Field (DOF) that is not more than 20% of the vertical height of the cells suspension when settled on said base surface.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
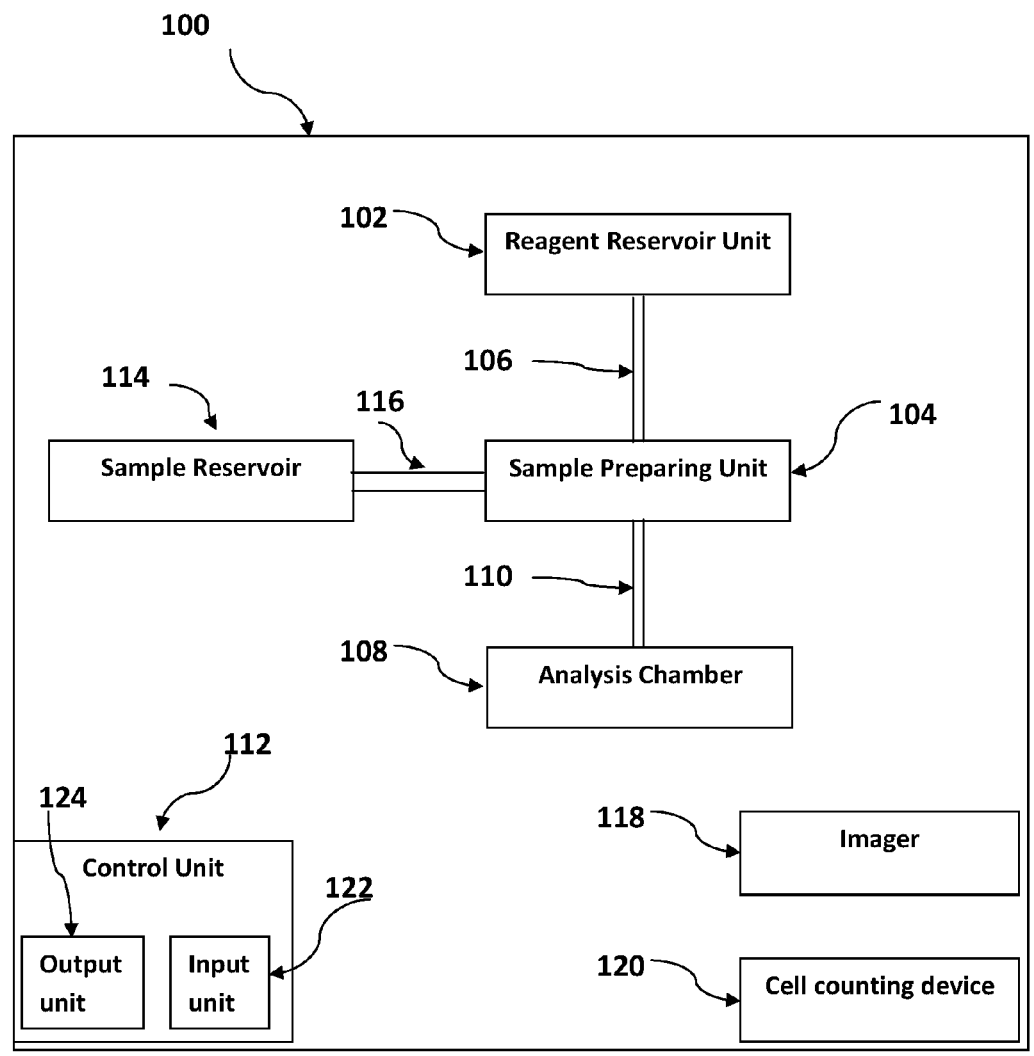
FIGS. 1A-1C illustrate components of a system in accordance with non-limiting embodiments of the present disclosure and a carrier to be used in accordance with some embodiments.

The present disclosure is based on the understanding that there is a need in the art of cell preparates for providing cells in a monolayer in a quick (in a scale of seconds or few minutes) and reproducible method so as to allow quick imaging of small objects in a cell sample, in particular, a blood sample. To this end, the inventors have developed a simple method that does not necessitate the use of expensive equipment, or to wait until the sample dries before microscope examination.

Specifically, the present invention provides a method comprising introducing a cell suspension comprising red blood cells, onto a base surface of a carrier having a vertical height (H) being greater than or equal to a vertical depth (h) of said cell suspension when on said base carrier, the cell suspension comprising a cell concentration (C) being determined by the function:

$$C=F/(h*pi/4*d^2)$$

(F) being a desired base surface coverage; and (d) being an average cell dimension of the cells in the cell suspension;

allowing the cells in the cell suspension to settle on said base surface of the carrier to form on the base surface of the carrier a monolayer of cells;

acquiring at least one microscope image of at least a portion of the monolayer of cells, wherein said at least one microscope image is obtained by a microscope to Depth Of Field (DOF) that is not more than 20% of the vertical height of the cell suspension when settled on said base surface.

Optionally, cell concentration C may be calculated using the carrier's vertical height H as an approximation of the sample's vertical depth h, when they are assumed to be approximately equal, such as when filling up the carrier or a chamber thereof with the sample.

A blood sample may contain a variety of cells, including red blood cells, platelets and macrophages. As such, in the context of the present disclosure, when referring to d it is to be understood as meaning the average dimensions of the cells in the sample, taking into consideration the different dimensions of the variety of cells therein. Since the vast majority of cells in a blood sample are RBC, d can be taken in some embodiments to be the average dimension of the RBC. The dimension (d) is provided in mm. The value of d may be determined for example by spectroscopy or from the literature. For example, the average diameter of a human RBC is 6.2-8.2 μm (0.0062-0.0082 mm).

In the above function for determining the cell concentration C, pi is the constant defining the ratio of a circles circumference to its diameters and is roughly equal to 3.14159;

The base surface coverage F as used herein, defines the percent of base surface area that is covered by cells after settling thereupon, and for the sake of illustration, when F=1 or near 1, when 100% or almost 100% of the cells are completely covering the base surface. When F=0 there are no cells on the base surface. In the context of the present disclosure, a high F (namely, closer to 1) enables rapid visualization of a greater number of cells while a low F (namely, closer to 0) enables a clear distinction between the different cells and in some embodiments may also enable more accurate prediction.

In one embodiment, the average base surface coverage is between 40% (F=0.4) and 90% (F=0.9). In some other embodiments, the average base surface coverage is between 40% and 60% (F being between 0.4 and 0.6).

The vertical depth h may be dictated by a desired minimal or maximal time interval allotted for sedimentation of the cells on the surface base. There is a direct relation between the height (the vertical depth) and time needed for the cells to settle on the base. In some embodiments, for formation of monolayer in a short period of time (e.g. tens of seconds and up to only several minutes), h is in the range of 20 μm to 1000 μm. In some other embodiments, h is in the range of 25 μm to 600 μm or 30 μm to 250 μm or even 75 μm to 200 μm.

The cells to be images are blood cells (whole blood or RBC sample) comprising at least red blood cells (RBC). In some embodiments, the blood cells are human blood cells. In some embodiments the blood sample comprises at least one of white blood cells (WBC), bacteria and platelets.

Further, in some embodiments, the blood sample comprises at least 50% RBC. In some other embodiments, the blood sample comprises at least 75% RBC.

The average concentration of blood cells in a blood sample withdraw from a living entity is known in the art. For example, the highest normal red blood cell (RBC) concentration in blood for women is 4.2 to 5.4 million/μl, for men is 4.7 to 6.1 million/μl and for children is 4.6 to 4.8 million/μl. When using a concentration known in the literature, it may be useful to take an average value or a maximum normal value and use it as a base value for dilution so as to obtain the desired concentration C. For example, for a human blood sample a value of about 6M cells/μl may be used. Alternatively, the cells in the blood sample may be counted or estimated (manually or automatically, as known in the art) before dilution and/or after to as to have a precise cell count for a given sample.

The desired concentration C of the cell suspension is such that if a volume of the cell suspension is placed on the base surface of a carrier such that the cell suspension has a determined or estimated vertical depth, and all or practically all cells are allowed to settle on the surface of the carrier, a monolayer is formed on the surface with no or little overlap between the cells.

The vertical depth h of the cell suspension may be determined or imposed or estimated. For example, when introducing the cell suspension onto a base surface of a carrier having a vertical height H, the maximum value of h is equal to H. Thus the vertical depth h of the cell suspension may be assumed to equal the vertical height H of the carrier, when the carrier is essentially completely filled by the cell suspension. If a smaller amount of the cell suspension is introduced onto the base surface, the vertical height H will not be completely filled, and hence the vertical depth h may be calculated or estimated based on the degree of filling and/or by dividing the volume of the cell suspension by the surface area which it covers.

Settling of the cells on the base surface of the carrier may take from several seconds to several minutes, for example without applying an external force (e.g. mechanical or centrifugation) to affect the process. To this end, the method provides a period of time between introducing the cells onto the carrier and acquiring the image to allow the cells to settle and form the monolayer. In some embodiments, the period of time is for not more than 5 minutes, at times, not more than 2 minutes, or even not more than 90 seconds, after which a desired monolayer is formed on the surface of the carrier's base. In some embodiments, settling involves maintaining the base surface in a horizontal position, and a time interval of between 20 seconds to 5 minutes following introduction of the cell suspension over said base surface. The time interval being, at times, dictated by the height of the sidewalls of the carrier (vertical height (H)) and the vertical depth h of the suspension (i.e. minutes per mm of h). During this time interval the carrier may be maintained essentially motion free. In some embodiments, the time interval until a monolayer is formed is not less than 20 seconds, at times, not less than 30 seconds.

In the context of the present disclosure, when referring to "monolayer" of cells it is to be understood as encompassing the distribution of cells on a surface as an essentially single layer, where at least 50%, at times at least 60%, 70%, 80% or even 90% of the cells are in direct contact with the base surface of the carrier and not more than 20%, at times no more than 10% or even no more than 5% of the cells overlay each other (i.e. no more than 20% of cells lie, partially or completely, one on top of another). Further, when referring to a "monolayer" it is to be understood that at least 5%, at times, at least 10% or even at least 20% of the cells touch each other on the safe base surface.

To provide a monolayer of cells, the sample of cells needs to be introduced onto the carrier at the desired concentration C. At times, the cells to be introduced onto the carrier are already provided with the concentration C, albeit, at times, the concentration of the cells is such that requires dilution.

In order to obtain the concentration C of the blood cells in the sample (which typically mostly RBC), the cells sample may be diluted. As such, and in accordance with some embodiments, the method comprises diluting the blood sample by a dilution factor (D) to provide a cell suspension.

Factor D may be calculated based on the desired concentration C and the concentration of the cells before dilution ($C_0$), as follows:

$$D = \frac{C_0}{C}$$

Since the desired concentration C is may be calculates as $$C = F/(h*pi/4*d^2).$$

As such, Factor D may be calculated using the equation:

$$D = \frac{C_0}{F/(h*pi/4*d^2)}$$

The concentration of cells before dilution ($C_0$) may be based on counting the cells in the sample. Counting may be performed by any technique known in the art, including, without being limited thereto, a counting chamber (hemocytometer), plating methods, spectrophotometry, flow cytometry, Coulter counter, as well as by image analysis techniques. At times, use may be made of information from literature. For example, the highest normal red blood cell (RBC) concentration in blood for women is 4.2 to 5.4 million/μl, for men is 4.7 to 6.1 million/μl and for children is 4.6 to 4.8 million/μl. When using a concentration known in the literature, it may be useful to take an average value or a maximum normal value and use it as a base value for dilution. For example, for a human blood sample a value of about 6M cells/μl may be used. In such cases, D may be selected to ensure that the vast majority of normal samples will be within a desired range of F. It is noted that dilution by dilution factor D may be performed in one or more dilution steps, so long as the total dilution is by factor D (or the final cell concentration equals C).

As such, in order to obtain a monolayer of blood cells comprising RBC in accordance with the present disclosure, the following are taken into consideration:

For a concentration of blood cells in a μl of a blood sample $C_0=6,000,000$ ($C_0$ in a normal blood sample is 4,000,000 to 6,100,000 cells/μl)

For an average diameter of the cells in the blood d=0.0075 mm;

For a carrier with a vertical height H=0.2 mm and a suspension having vertical depth h=0.2 mm;

For a desired base surface coverage of F=0.5 (50% of the surface is covered by a monolayer of cells)

The dilution Factor D is calculated using the above equation would thus be about 100.

Similarly, under the same conditions but with a carrier having a vertical height H=0.1 mm and a suspension having vertical depth h=0.1 mm, the dilution factor D is calculates using the above equation, and would thus specifically be about 50.

In some embodiments, the dilution is by a factor D of between about 50 to about 300. In some other embodiments, the factor D is between about 75 and about 200. In yet some other embodiments, the dilution is by factor D of about 100.

In yet some other embodiments, the dilution of the blood sample comprising RBC is to obtain a cell concentration C in the cell suspension such that after setting on the base surface of the carrier and forming the desired monolayer, the cells' density on the surface is between about 10,000 to about 30,000 cells per $mm^2$.

Dilution (by factor D) may be performed using any cell diluting agent, such as a buffer known to be used in the art of cell biology which will be isotonic at the time of sample preparation. Non-limiting examples of buffers include Phosphate Buffered Saline (PBS), buffer comprising 4-(2-hydroxyethyl)-1-piperazineethanesulfonic acid (HEPES), 2-(N-morpholino)ethanesulfonic acid (MES), piperazine-N,N'-bis(2-ethanesulfonic acid (PIPES), N-(2-Acetamido)-2-aminoethanesulfonic acid (ACES), 3-(N-morpholino)propanesulfonic acid (MOPS), 2-[[1,3-dihydroxy-2-(hydroxymethyl)propan-2-yl]amino]ethanesulfonic acid (TES), 2-(Bis(2-hydroxyethyl)amino)acetic acid (Bicine), 3-[4-(2-Hydroxyethyl)-1-piperazinyl]propanesulfonic acid (HEPPS or EPPS), 3-[[1,3-dihydroxy-2-(hydroxymethyl)propan-2-yl]amino]propane-1-sulfonic acid (TAPS), N-(2-Hydroxy-1,1-bis(hydroxymethyl)ethyl)glycine (Tricine), Ethylene-diamine-tetra-acetic acid (EDTA), Sodium Chloride (NaCl), Tris(hydroxymethyl)aminomethane (Tris)

The formation of a monolayer upon or following introduction of the cell suspension into the carrier may be performed with no additional intervention (e.g. no centrifugation or smearing). This may be performed simply by allowing the sample to rest for a short period of time, (namely, from seconds to several minutes) on a flat horizontal surface of the carrier.

Once the cells are settled on the base surface of the carrier and a desired monolayer is formed (as a result of the desired cell concentration upon said introduction), at least one microscope image of the cells is acquired. The image is of at least part of the surface covered by the cells.

Microscopic imaging techniques are well known in the art and include, inter alia, optical microscopy, fluorescent microscopy, and the like. In some embodiments, the microscopic imaging is for the purpose of diagnosis. Optionally, both one or more florescent images and one or more brightfield images are taken.

The inventors found that in order to detect objects within a monolayer of blood cells obtained from a cell suspension of the desired concentration C (as discussed above) one should select a particular range of Depth of Field (DOF) to allow clear visualization of the small object within the population of blood cells.

DOF is known as the distance between the nearest and farthest objects in a scene that appear acceptably sharp in an image. DOF is mostly a property of the microscope's objective lens and the magnification, the latter being determined by the resolution of interest. For example, for an object being about 1 μm in dimensions (e.g. schizonts or some platelets), a resolution of at least 0.5 μm would normally be required; similarly, for an object of about 2 μm in dimension, a resolution of at least 1 μm would normally be required. This also determines the magnification, and a magnification of at least 20× would be used for a resolution of about 0.5 μm, while a magnification of at least 10× would be used for a resolution of about 1 μm. In this connection, it is noted that a lens is chosen to provide a desired magnification. Lens is characterized by a numerical aperture (NA). For example, a lens for 20× magnification may have a numerical aperture (NA) of about 0.4-0.5, while a lens for 10× magnification may have a significantly smaller NA.

According to Shillaber equation, DOF relates to NA for a given wavelength of light (λ) and medium refraction index (Ri):

$$DOF = \frac{\lambda \sqrt{Ri - (NA)^2}}{(NA)^2}$$

Below are provides non-limiting examples of DOF for several commercially available microscope objectives using 500 nm light and air as the medium (Ri=1.00) between microscope objective and object:

| Magnification | Numerical Aperture (NA) | Depth of Field (DOF) |
|---|---|---|
| 4× | 0.10 | 50 |
| 10× | 0.25 | 7.7 |
| 20× | 0.40 | 2.9 |
| 40× | 0.65 | 0.9 |
| 60× | 0.85 | 0.36 |
| 100× | 0.95 | 0.17 |

To obtain the DOF of interest, the method may comprise, in accordance with some embodiments, selecting a microscope objective lens that provides said DOF, wherein said lens permits acquiring an image of at least one object being no more than 3 μm long at any dimension thereof.

In some embodiments, said lens permits acquiring an image of at least one object having a height with respect to said base surface of no more than 3 μm.

The inventors have surprisingly found that preparing a monolayer for high resolution microscopy does not necessitate placing the blood in special carriers as known in the art, which often have a vertical height H of 15 μm or less. Instead, by providing a diluted cell sample and inserting it onto the base surface of a carrier having a larger vertical height H a monolayer may be formed, and this monolayer is well dispersed and may be imaged at a very high resolution which is unexpected in view of the relatively large vertical depth h of the suspension when placed on the base surface.

The inventors have successfully determined that such monolayer of blood cells once formed having the desired surface coverage of at least 40% cells (F>0.4), it is sufficient for use at a DOF should that is even 20% or less of the vertical height h of the suspension once placed on the base surface, at times, no more than 15% the vertical height, or even not more than 10% the said vertical height. To this end, the inventors have determined that the vertical height h may be within the range of 30 μm to 300 μm, as further discussed below.

As such, and as an example only, for an object having a size of about 1 μm (e.g. schizonts and some platelets), a resolution of at least 0.5 μm is normally required, for which a magnification of at least 20× is normally characterized by the numerical aperture (NA) of about 0.4-0.5. A numerical aperture of 0.4-0.5 may provide a DOF of 2.9 μm which is not more than 20% of a 30-300 μm vertical height h being defined herein for the suspension when placed on the surface base.

Similarly, and as a further example only, for an object having a size of about 2 μm, a resolution of at least 1 μm would normally be required, and a magnification of at least 10× would thus be used. For this magnification, a lens with NA of about 0.2-0.25 may be used and this correlates with a DOF significantly larger than that of the aforementioned 20× objective, but still, not more than 20% of a 30-300 μm vertical height h being defined herein for the cells when settled on the surface base.

In line with the above and in accordance with some embodiments of the invention, imaging is performed at a DOF being between about 0.5 μm and about 10 μm; at times, between about 0.5 μm and 5 μm.

The above conditions for acquiring the microscope image allow for the detection of small objects being smaller than red blood cells, such as platelets and pathogens, within a blood sample. In accordance with some embodiments, the microscope set provides a DOF that allows acquiring an image (one or more) of at least one object being no more than 3 μm long at any dimensions thereof.

As noted above, to allow imaging of these smaller objects, a monolayer of the larger cells in the sample is required, and this typically requires diluting a raw blood sample (optionally comprising an anticoagulant or EDTA) before introducing onto the carrier. However, in addition to dilution, the cells may be treated (e.g. mixed) with one or more other reagents, such as stains. Staining may be performed before, during or after placing the sample in the carrier. The stain may be any dye, probe or substrate suitable for cell staining, including fluorescent dyes, and if a plurality of dyes, probes or substrates is added, some or all of the stains may be a fluorescent dye. In one embodiment, at least one stain is a fluorescent dye. In some embodiments at least one dye is included in a diluting agent.

When referring to a stain it is to be understood as encompassing any chemical or biological substance that is capable of staining a component of a biological cell, to enhance contract and highlight structures of the stained object, be it a cell or part of a cell. The stain may have a class preference or specificity, e.g. may have preference or specificity to staining of nucleic acids and among the nucleic acid, to DNA or RNA, preference or specificity to amino acids, to lipids, carbohydrates etc.

When referring to preference or predominant staining it is to be understood that the stain marks (stains) a cellular component in a particular color or fluorescence that is at least twice, three times, four times or even 10 times greater in its intensity than its staining intensity to another cellular component at that same color or fluorescence spectrum.

In some embodiments, when referring to preference or predominant staining it is to be understood that the stain has affinity (molecular attraction) to one cellular component (in the particular color or fluorescence spectrum) that is at least twice, three times, four times or even 10 times greater in its affinity to another cellular component (at that same color or fluorescence spectrum).

In some further embodiments, when referring to preference or predominant staining it is to be understood that the staining of the one component by the stain is stable or has more stability as compared to its staining of other components. Stability may be understood to mean that the staining produced by the stain remains substantially consistent for at least 30 minutes after being brought into contact with the stain, at times, at least 1 hour, 2 hours or even 5 hours after staining the sample with the stain having preference to the one component. Alternatively, stability may be understood to mean that the staining produced by the stain remains substantially consistent during exposure to light (e.g. light used for fluorescence excitation) for at least 0.25 seconds, 1 second, or even 15 seconds of exposure.

In this context, it is to be understood that the stain having preference to, for example, DNA, may also stain other cellular components but with lower attraction or lower intensity or with a different florescence response (excitation spectrum and/or emission spectrum) such that it allows the greater enhancement of the one component to which the stain has preference. For example, a stain may predominantly stain DNA, however, under some other conditions the same stain may stain RNA.

In some embodiments, the stains are not cell type specific. In other words, the stain may not be specific to a particular pathogen or to a particular stage of the life cycle of a particular pathogen or to a particular cell of the host being infected therewith and will stain a cell component irrespective if its origin, e.g. a DNA sequence or structure per se, an RNA sequence or structure per se, protein per se, etc.

There are a variety of stains that may be used in accordance with the present disclosure. In some embodiments, the stain is a chromophore or fluorophore.

Stains such as the Giemsa stain (CAS 51811-82-6) are known as chromogenic—their effect is to provide color or opacity to the sample and are visible, for example, in bright field microscopy.

In some embodiments, the stain provides fluorescent staining of the sample. Fluorescence is visualized by illuminating the sample with an "excitation" spectrum of light, which results in an "emission" at a distinct spectrum of light.

In some embodiments, the stain is a fluorochromatic dye selected from the group consisting of Acridine Orange (AO, N,N,N',N'-Tetramethylacridine-3,6-diamine, green staining for DNA, red stain for RNA), Giemsa stain which is known as a solution of methylene blue (3,7-bis(Dimethylamino)-phenothiazin-5-ium chloride), eosin (CAS Number 17372-87-1) and Azure B (Trimethylthionine chloride), Ethidium Bromide (3,8-Diamino-5-ethyl-6-phenylphenanthridinium bromide), Hoechst family ($C_{25}H_{26}N_6R$, with R representing a variety of possible substituents, such as, without being limited thereto, —OH (Hoechst 33258); —$CH_2CH_3$ (Hoechst 33342), —$N(CH_3)_2$ (Hoechst 34580), —$SO_2NH_2$ (Hoechst S769121)), DAPI (4',6-diamidino-2-phenylindole), propidium iodide (2,7-Diamino-9-phenyl-10 (diethylaminopropyl)-phenanthridium iodide methiodide), SYBR family, YOYO, DRAQ family, SYTOX family, TOTO family, crystal violet (Tris(4-(dimethylamino)phenyl)methylium chloride), any and all molecular beacons, adjacent probes, nuclease probes, light up probes, substrate based probes Hematoxylin stains, Safranin (azonium compounds of symmetrical 2,8-dimethyl-3,7-diamino-phenazine), acid-Schiff stains, Masson's stain, Prussian blue and any combination thereof.

In one embodiment, more than one stain is used. For example, the sample may be stained with two or more stains, comprising at least one stain predominantly staining DNA to thereby provide differential staining between DNA and at least one other cellular component being different from DNA. Alternatively, a single stain may be used, which is excited at two different wavebands, thus providing two different colors. For example, stains such as AO provide different fluorescence spectra for different cellular components. When AO stains DNA at neutral pH, it has an excitation maximum at 502 nm (cyan) and an emission maximum at 525 nm (green); when it stains RNA at neutral pH, the excitation maximum shifts to 460 nm (blue) and the emission maximum shifts to 650 nm (red). As such, it allows differential staining between DNA and RNA, depending on the excitation wavelength and conditions of the sample.

When referring to a combination of two or more stains, it is to be appreciated that the two or more stains may be added to the sample simultaneously or in sequence.

The method disclosed herein provides the detection of a pathogen in the blood sample. Thus, it is not necessary that all cells be infected and the method is applicable also when only a portion of the cells (even a single cell) is infected by a pathogen. The pathogen may be any infectious microorganism.

In some embodiments, the pathogen is a eukaryotic parasite, and the parasite may be a one cell parasite.

In some embodiments, the parasite is a blood protozoa selected from the genus consisting of *Trypanosoma* (causing Chagas disease and African sleeping sickness); *Plasmodium* (causing Malaria); *Toxoplasma* (causing Toxoplasmosis); *Babesia* (causing Babesiosis).

Specifically, when referring to *Plasmodium* it is to be understood as encompassing at least any member of the group consisting of *Plasmodium falciparum* (*P. falciparum*), *Plasmodium vivax* (*P. vivax*), *Plasmodium ovale* (*P. ovale*), *Plasmodium malariae* (*P. malariae*), and *Plasmodium knowlesi* (*P. knowlesi*).

In some embodiments, pathogen is understood to mean a particular stage of the life cycle of a particular pathogen or group thereof. For example, the invention disclosed herein can be applied specifically to the detection of trophozoites, schizonts or gametocytes of *Plasmodium* species or *P. falciparum* in particular.

The carrier to which the sample (typically diluted) is introduced is defined by its base surface and sidewalls. The sidewalls define the carrier's vertical height (H) which is to be equal or greater than the vertical depth (h) of a cell sample when introduced onto the base surface of the carrier (i.e. into the carrier). As such, the carrier may be any unit having an internal void defined by the base surface and the sidewalls and which is biocompatible with biological cells. Where referring to biocompatible it should be understood that the cells at least remain intact, and that optionally viability and/or functionality are also essentially maintained. The carrier may be provided in different forms.

In some embodiments, the carrier is of a kind suitable in diagnostic imaging. Examples of carriers applicable in accordance with the present disclosure include microfluidic channels and a well, such as in a multi well plate.

The carrier to be used with the invention may be of different kinds and may have different forms, either a commercially available carrier, or one that is specifically designed, as long as it has a vertical height of no less than about 20 µm and is capable of holding a cell sample with a vertical depth h (the vertical depth being the distance between the top surface of the sample in the carrier and the base surface of the carrier) and, not mandatorily, no more than 1000 µm.

The carrier may have an open end, e.g. open top (e.g. a base with side walls), with or without a compatible cover, yet it can be in the form of a closed cavity with a dedicated narrow inlet for introducing the cells (e.g. in the form of a bottle or microfluidic chamber). In some embodiments, the cell suspension is introduced into the chamber by capillary forces. At times, one or more inner portions of the carrier may be coated or treated, to become hydrophilic and the capillary forces are increased.

In some embodiments, the carrier is a well, such as those used for cell culturing, and the well may be covered with a compatible cover. Using a cover applied on the cell suspension may overcome the capillary effect of the walls of the well on the sample, when the latter is introduced in small volumes that may lead to a non-even distribution of the sample in the well.

The top surface (whether fixed or removable) may extend parallel to the base surface or to only part thereof. Also, it may be applied before or after the introduction of the cell suspension onto the base surface.

The carrier or at least the base surface of the carrier may include means for physical and/or chemical immobilizing the cells being introduced Immobilization may be by the use of cell adhesives. In addition or alternatively, the base surface may be electrically charged to attract cells. For example, in the case of RBCs, by treating the base surface with poly-lysine which has a positive charge, this will attract the negatively charged RBCs and help in acquiring a more stable monolayer. Other examples for compounds that may be used for electrically charging the surface are aminosilane, epoxy, aldehyde and glutaraldehyde.

When a removable cover is used, it may apply forces onto the sample that has been introduced on the base surface, and by this to expedite the sedimentation process. On the other hand, the cover might cause rupture of the cells (for example by sheer weight). One way to prevent or minimize the cells damage is by the use of spaces of size compatible to the average cell's size.

Additionally, the spacers may also act to create a more uniform layer thickness and thus a more uniform distribution of cells on the base surface of the carrier.

These spaces may be in the form of microparticles or beads, acting as pillars or supporting bodies holding the cover over the cell suspension, without causing any damaging pressure on the cells. Exemplary shapes of spaces may include, without being limited thereto, spacers having a cylindrical shape, with a circular cross section, oval cross section, hexagonal cross section, a star shape cross section. Further, the spacer may be in the form of a disc, or may be in the form of beads with polygonal surface.

The dimensions of the spacers dictate the space between the base surface and the cover (top surface). Without being limited thereto, the dimensions of the spacers are such that a space of 50 μm, at times 100 μm and further at times 200 μm between the two surfaces are formed. This is obtained by using spacers with a cross sectional diameter along their smaller axis in the range of 50 μm, at times 100 μm and further at times 200 μm. Optionally, the spacers have a diameter that is comparable to the height of the cells in the sample. Thus, they may prevent a cover from pressing the cells to an extent that is damaging. Accordingly, the diameter of the spacers may be 2-3 μM. When using spacers in the form of beads, the space may be dictated by the beads radius, being, for example, in the above ranges.

The spacers may be made of any biocompatible material. For example and without being limited thereto, latex, silicon, glass, plastic etc. Further, the spacers may be transparent, semi transparent or non-transparent. They may also be of a type only visible under a given wavelength or band of wavelengths.

The number of spacers used may be chosen so that it ensures the top and base surfaces of the carrier to be substantially parallel. To this end, it is sometimes preferable that the spacer units used are of essentially uniform size. To maintain a fixed height between the surfaces, the spacers may be fixed to at least one of the surfaces, e.g. the base surface. This may also reduce the number of spacers needed.

In some embodiments, an amount of spacers (e.g. beards) in a range of 1 spacer per $mm^2$ to 2500 spacers per $mm^2$ is used.

In some embodiments, the space between the base surface and top cover may be dictated by the use of a spring affixed to at least one of the surfaces.

Spacers may be used in the process of constructing a carrier with any given vertical height (e.g. equal to the vertical depth of the fluid sample h). For example, spacers may be mixed in with glue that binds the top and bottom surfaces of the chamber (mixing beads in glue as used for example in liquid crystal displays (LCD)).

The present disclosure also provides a kit, the kit comprising:

a carrier comprising a base surface and a vertical height (H); and instructions for performing the steps of:
providing a cell suspension from a blood sample comprising red blood cells, the cell suspension being of a cell concentration (C) determined by the function:

$C=F/(h*pi/4*d^2)$.

(F) being a desired base surface coverage; and (d) being an average cell dimension of the cells in the cell suspension;
introducing the cell suspension of the desired concentration C onto the base surface of the carrier, the cell suspension having said vertical depth (h) when in said carrier, said vertical depth (h) being smaller or equal to the vertical height (H);
allowing the cells in the cell suspension to settle on said base surface of the carrier to form onto the base surface a monolayer of cells;
acquiring at least one microscope image of at least a portion of
wherein said at least one microscope image is obtained by setting the microscope's magnification to a Depth Of Field (DOF) that is not more than 20% of the vertical height of the cell suspension when settled on said base surface.

The kit and the instruction therein allow performing the method as disclosed herein.

Also provided by the present disclosure is a system for imaging a blood sample, the system comprising:
One or more reservoir units for holding, respectively, one or more sample treatment agents comprising at least one blood cells diluting agent;
a blood sample preparing unit being in fluid communication with said one or more reservoir units and configured to receive a blood sample comprising red blood cells and amount of at least one blood cell diluting agent and to form therefrom a blood cells suspension, the amount of said at least one cell diluting agent being determined so as to dilute said sample of cells by a dilution factor (D) so as to provide a cell concentration (C);
a microscope image acquisition unit for acquiring at least one image of the blood cells suspension when on a base surface of a carrier, the carrier having a vertical height (H) being greater or equal to a vertical depth (h) of said cell suspension when on said base surface;

a control unit being configured to:
provide dilution factor D of diluting said sample, factor D being a function of the desired base surface coverage (F), the average cell dimension d of cell blood cells, and the vertical depth h of said suspension of cells that provides a monolayer of the cells when settled on said base surface of the carrier; and
acquire at least one microscope image of the cell suspension by a microscope set to a Depth Of Field (DOF) that is not more than 20% of the vertical height of the cells suspension when settled on said base surface.

In some embodiment, the control unit is configured to determine the dilution factor based on parameters either being accessed or introduced or already stored within the system. To this end, the control unit is configured to access such parameters, including those indicative of a desired base surface coverage.

The system may also comprise an analysis chamber for holding a carrier having a vertical height (H) being greater or equal to said vertical depth (h), said analysis chamber being in fluid communication with said sample preparing unit and configured to receive into said carrier an amount of cells having a concentration C.

When referring to fluid communication it is to be understood as including a conduit, e.g. a pipe, a tube connecting one unit to another, as well as any fluid transfer means such as robotic fluid withdrawal and discharge devices or pipettes.

As part of the system disclosed herein, the said one or more treatment agents may comprise, in accordance with some embodiments, one or more stains. At least one of the at least one diluting agent comprises the one or more stains. In other words, the at least one stain may be mixed with the dilution buffer prior to diluting the blood sample.

In some embodiments, at least one of the stains is a fluorescent stain. In some embodiments, the at least one stain is selected from the group consisting of acridine orange, Hoechst family, molecular beacon, Sytox or DAPI.

In addition and in accordance with some embodiments, the system comprises a fluid withdrawal mechanism for withdrawing a sample of blood cells from a blood source and introduce said sample of blood cells into said sample preparing unit.

Further, in some embodiments, the system comprises a cell count unit for counting cells received by the cell preparing unit.

In yet some further embodiments, the system comprises a sample preparing unit and the latter may comprise an agitating unit configured to uniformly distribute the cells in the cell suspension.

As appreciated, the system may also comprise, in accordance with some embodiments, an output port for outputting said at least one image or data corresponding to the image, for example to an associated display and/or to a remote location.

Yet further, in accordance with some embodiments, the system may comprise a memory unit accessible by the control unit and comprising data indicative of said input parameters. The data may comprises for one or more input parameters a cell type in the blood sample and said data is accessible by said control unit. The data may also comprise said for one or more input parameters a cell type in the blood sample and said data is accessible by said control unit.

Further, at times, the system may comprise a processor configured to analyze said at least one microscope image to determine based thereon presence or absence of a pathogen in said cell suspension.

Preferably, the system is for detecting one or more parasites within a blood sample.

The system also comprises a control unit. In accordance with some embodiments, the controller is configured to cause the microscope image acquisition unit to acquire a plurality of microscope images of the monolayer, at least two of which are provided under different conditions, said conditions comprising imaging different portions of the monolayer (or base surface) and different illumination conditions.

Reference is now made to FIG. 1A which is a schematic illustration of components of a system 100 in accordance with an embodiment of the present disclosure.

System 100 includes a reagent reservoir unit 102 for holding a sample treatment agent and a sample preparing unit 104, the reagent reservoir unit 102 comprises a diluting agent and is in fluid communication with the sample preparing unit 104 through conduit line 106.

Figure 1B:
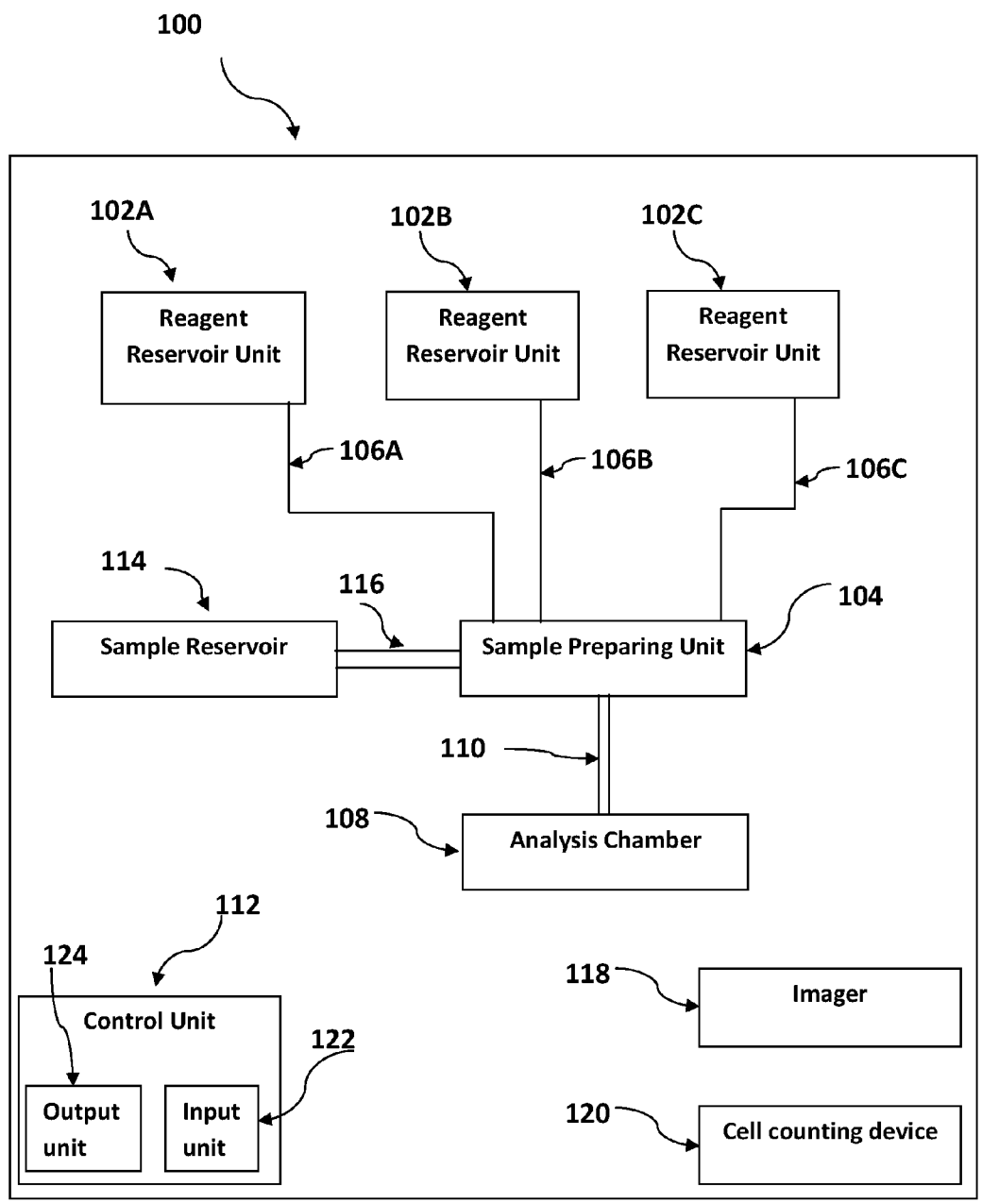

While system 100 is illustrated as including a single reagent reservoir unit 102, as shown in FIG. 1B, the system may similarly be configured to include a plurality of reagent reservoir units 104A, 104B, 104C, each for holding the same or different agent and being in fluid communication with the sample preparing unit 104 via an array of conduits 106A, 106B and 106C. Each reagent reservoir units 104A, 104B, 104C may include the same diluting agent, in a different concentration, a different diluting agent, or different treatment agents, such as a stain, a dye, a spacer agent, as further discussed below.

Sample preparing unit 102 is configured to receive a sample of cells and, if required, from reagent reservoir unit 104, an amount of cell diluting agent. In operation, the biological sample of cells in the sample preparing unit 102 is preferably is in the form of a cell suspension. To this end, the sample preparing unit may be equipped with a mixing mechanism, such as a gentle stirrer or shaking/agitation platform etc (not illustrated), so as to cause the cells to suspend in the medium they are in (i.e. prevent settling of the cells in the sample preparing unit).

Figure 1C:
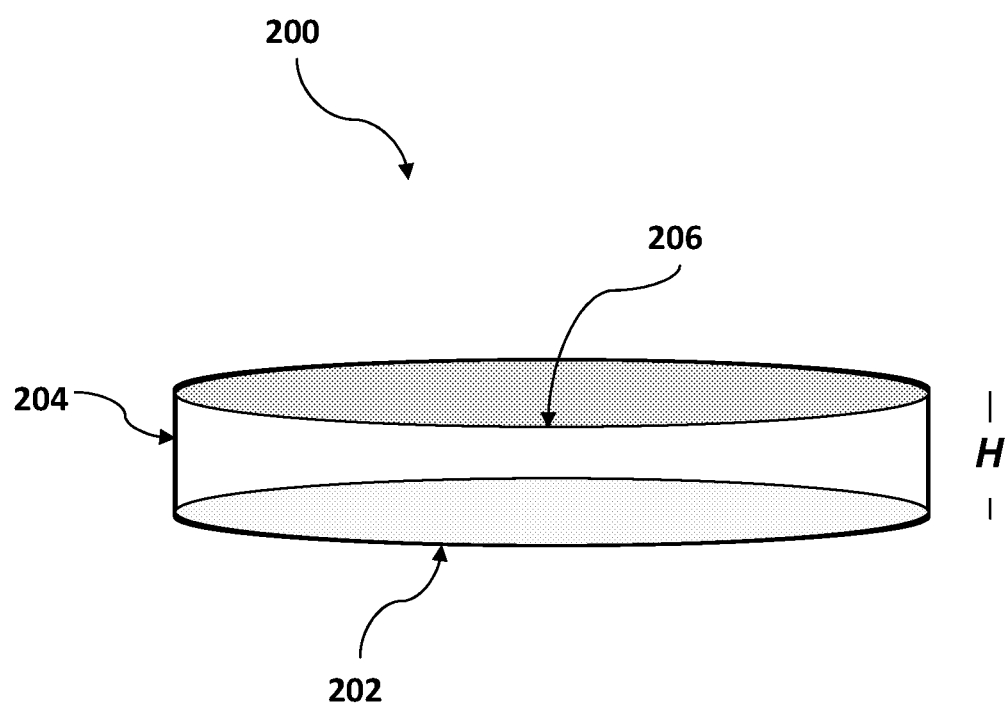

System 100 also comprises an analysis chamber 108 for holding a carrier 200 illustrated in FIG. 1C as a well with having a base 202 side walls 204, an open top 206, and a vertical height (H).

The analysis chamber 108 in FIGS. 1A and 1B is in fluid communication with the sample preparing unit 104 via conduit line 110 and is configured, upon operation and when holding a carrier 200 in place, to receive into carrier 200 an amount of cells, from sample preparing unit 104, the amount of cells being delivered at the desired concentration C. Notably, while System 100 is illustrated as including fluid communication lined, transfer of matter from one unit to the other may alternatively or additionally be accomplished manually, e.g. using transfer equipment such as a pipette and/or automatically, for example by a robotic arrangement.

System 100 also comprises a control unit 112 configured to receive, inter alia, input parameters regarding concentration of cells before dilution ($C_0$), an average dimensions (d) for said cells, and desired base surface coverage (F). This input may be introduced into control unit 112 manually, e.g. by a user interface (not illustrated), and/or by retrieval from a stored database. Control unit 112 is also configured to apply Factor D of dilution of the reservoir sample of cells by a diluting agent. Further, control unit 112 is configured to control operation of the components of the system, including delivery of a determined amount of diluting agent from a reagent reservoir unit 104 into the sample preparing unit 102, delivery of an amount of cells from the sample preparing unit 202 into carrier 200 when held in analysis chamber 108.

The control unit may also be equipped with a memory unit (not illustrated) operable to store one or more of the input parameters optionally in association with cell types and/or cell sources as well as a desired surface coverage (F) and desired Factor D as well as any other parameter for which storing is desired by the user.

At times, system 100 may also include a sample reservoir 114 for holding the cell source sample in its base (undiluted) concentration. The sample reservoir 114 is in fluid communication with sample preparing unit 102 via conduit line 116.

System 100 may also include or be associated with an imager 118 for imaging cells in carrier 200, after the cells are settled in the form of a monolayer on the base surface 202 of carrier 200; and in such embodiments, control unit 112 is further configured to actuate imager 118 to acquire at least one image of the cells in carrier 200.

Imager 300 may be any image acquisition device known in the art. In some embodiments, imager 118 is a microscopic camera (e.g. CCD).

Imaging may require, at times, dying of the sample prior to imaging. To this end, and as also mentioned above, in system 100 one or more of the reagent reservoir unit 102A, 102B or 102C etc. may include a staining reagent. At times, the stain in a reagent reservoir may be in fluid communication directly with analysis chamber 108 (not illustrated).

Further, at times, in system 100 one or more of the reagent reservoir units 102A, 102B or 102C etc may include a spacer reagent including for example, microparticles or beads as discussed above in a suitable buffer.

System 200 may also comprise or be associated with a cell counting unit 220 for counting the number of cells in the sample reservoir (i.e. to estimate the concentration of cells before dilution ($C_0$) and/or number of cells in the sample preparation unit (for the desired concentration C).

System 100 also includes fluid withdrawal mechanisms, such as pumps, and injectors (not illustrated) configured to withdraw fluid from the different reservoir units and inject the withdrawn fluid into sample preparation unit 104 and/or carrier 200 when in analysis chamber 108, and from sample preparation unit 104 into analysis chamber 108 as dictated by control unit 112.

System 100 may also comprise input and output utilities 122 and 124, respectively, introducing data into control unit 112 and for presenting at least one image or data corresponding to the at least one image obtained by the imager.

DESCRIPTION OF NON-LIMITING EXAMPLES

Example 1

Detection of *Trypanosoma brucei*

A mammalian blood sample (human) was assayed as follows for the presence of *Trypanosoma brucei*. Typically, such blood samples hold between 3,000,000 and 6,000,000 RBC's in each 1 μl ($C_0$). A cartridge having one main chamber was manufactured, whereby the height (H) of the chamber was 100 μM and the chamber could receive a volume of 1 μl.

The blood sample was diluted 50× (D) to have a surface coverage (F) of between 0.6-0.8 with a 1000 μl solution, containing 1% TRIS-EDTA 1 mM, 15 μl Hoechst 1 μg/μl, 2 μl acridine orange 1 μg/μl, 99% buffered saline. The sample was loaded into the chamber and the chamber was transferred to a microscope stage for imaging in both brightfield and in fluorescence at excitation 370 nm and 475 nm and emissions of approximately 433 nm and 517 nm, and 613 nm using an automated microscopy device. Sedimentation of the sample occurred at about 1 second per 1 μM height of the chamber (H), which is approximately 90 seconds.

Microscope images were acquired 1-2 minutes after introducing the blood into the chamber. The images were taken at a 20× magnification, with a depth of field (DOF) of about 2.3 μm for the florescent image (i.e. about 2.3% of the sample height).

Figure 2:
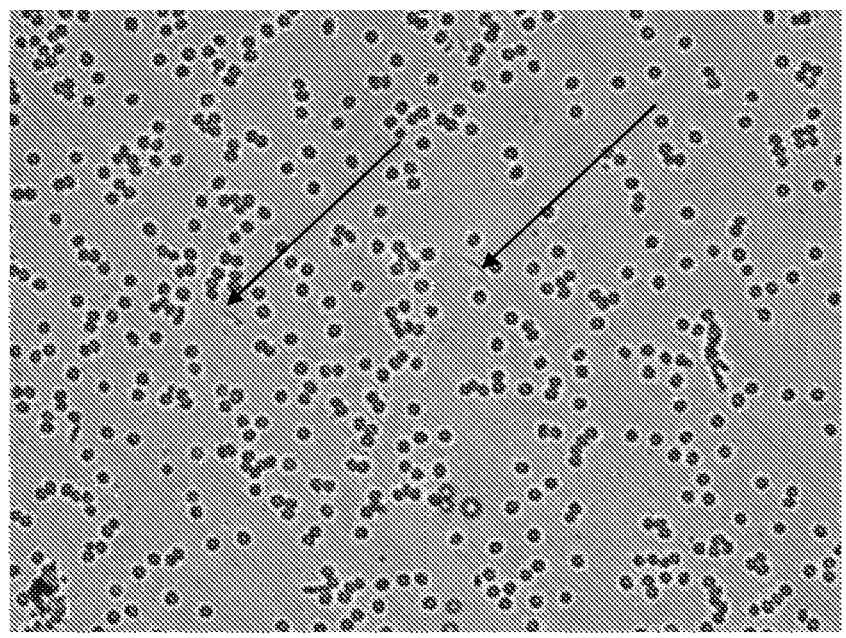
FIG. 2 is a microscope image of *Trypanosoma brucei* parasites from a peripheral blood sample, captured while *Trypanosoma brucei* parasites are identified (marked by arrows) in a monolayer obtained in accordance with an embodiment of the invention.
Figure 3:
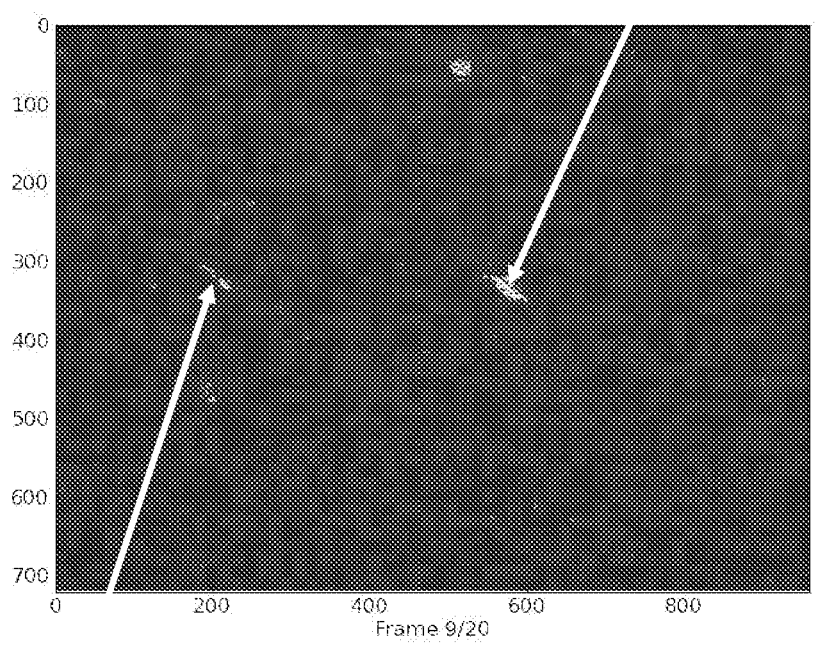
FIG. 3 is a florescent image of *Trypanosoma brucei* parasites from a peripheral blood sample, captured while *Trypanosoma brucei* parasites are identified (marked by arrows) in a monolayer obtained in accordance with an embodiment of the invention.

As seen in a brightfield image shown in FIG. 2, the cells formed a monolayer where some cells were touching and almost no cells were overlapping. As seen, the sample included predominantly red blood cells which covered about 70% of the surface (F≈0.7). In addition, *Trypanosoma brucei* were observed and marked by arrows. FIG. 3 depicts the same cells imaged fluorescently (excitation at 350 nm and emission measured at 461 nm) to specifically highlight *Trypanosoma brucei* against the background of red blood cells and allows their detection.

Example 2

Detection of *Plasmodium falciparum*

Staining Solution Composition

The purpose of this example stain solution is to identify live pathogen (e.g. *Plasmodium*) inside living blood cells. The solution comprises Hoechst 33342 (excitation 350 nm) and Acridine Orange (excitation 500 nm). The dyes were mixed with saline and Tris-EDTA to create an isotonic solution to keep red blood cells at physiological conditions during the stain and prevent them from lysing. This solution was used as a dilution solution thus potentially providing dyes and diluting the cells in a single step.

Stating Blood Sample for Detection of *Plasmodium*

Blood previously mixed with EDTA (or any other anticoagulant) was diluted in the above stain solution (~1:100). Within 10 seconds the blood was stained with the chemical dyes and giving off fluorescent signals between 450 nm and 550 nm when appropriately illuminated. The solution mixed with the blood was loaded into a plastic cartridge. After the blood cells settled they were scanned using LED fluorescent lights and a fluorescent microscope.

Hoechst was intended to stain DNA while Acridine Orange was meant to stain the RNA in the cells. In normal mature red blood cells there is no DNA or RNA, so mature red blood cells showing a positive stain may be indicative of an intracellular pathogen, such as malaria.

Detection of *Trypanosoma brucei*

An assay similar to that of Example 1 was performed with a blood sample suspected to be infected with *Plasmodium falciparum*. In general, a whole blood sample was diluted by a factor of 100 (1:100) in a fluorescent stain solution comprising Tris-Saline and the fluorescent dye Acridine Orange. The diluted cell sample/suspension was introduced into a chamber having a height (H) of about 200 μm and filled it up, thereby achieving a vertical depth of about 200 μm. The cells were then allowed to settle and form a monolayer.

Figure 4A:
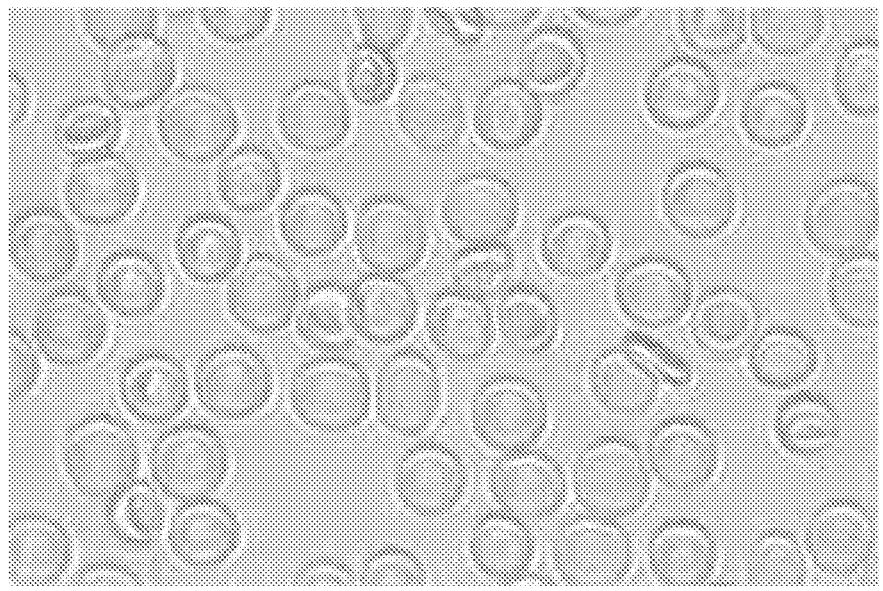
FIGS. 4A-4B show images of a blood sample obtained as a bright image of blood cells at 20× magnification with a monolayer coverage of 75% (FIG. 4A) and a corresponding fluorescent image stained with Acridine Orange fluorescent dye ($\lambda$=570 nm) at a depth of field of 2.3 μm (FIG. 4B) showing presence of a pathogen as indicated by an arrow.
Figure 4B:
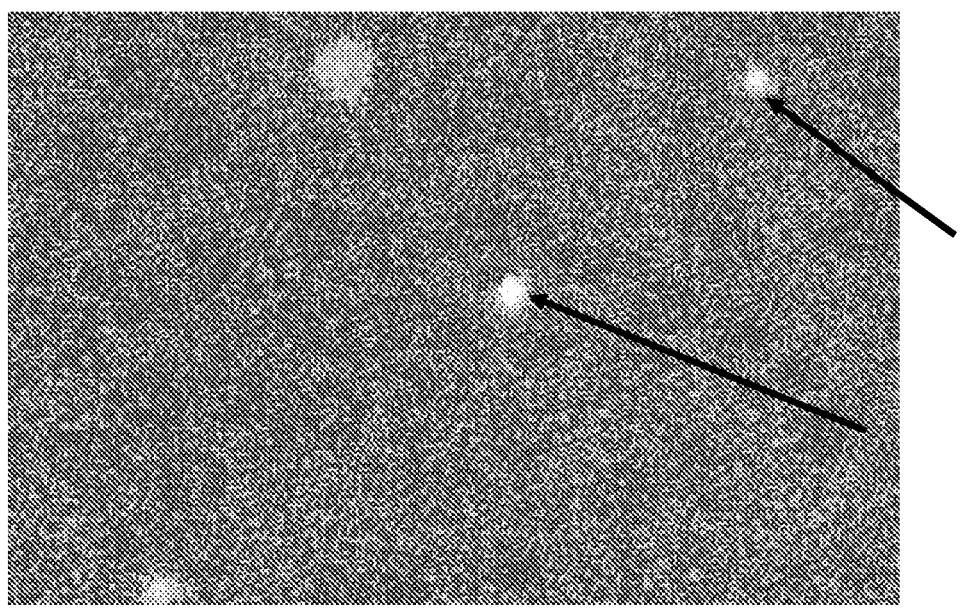

FIG. 4A shows a brightfield image at 20× magnification of the monolayer of cells, with an apparent surface base coverage of about 75% (F≈0.75). FIG. 4B shows a florescent image of the same cells of the diluted blood sample stained with the staining solution, showing in this image the stain by Acridine Orange (AO) fluorescent dye, and emitting fluorescence at 570 nm. The DOF was 2.3 μM (ca. 1.12% of the sample height (h)). The RBC depicted in this Figure had a maximal dimension of about 4 μM.

Detection of *Plasmodium* and Platelets in a Blood Sample

A differential detection between *Plasmodium* and platelets in a blood sample comprising red blood cells was also performed, using the same assay conditions and parameters as in the above FIG. 4A-4B.

Figure 5A:
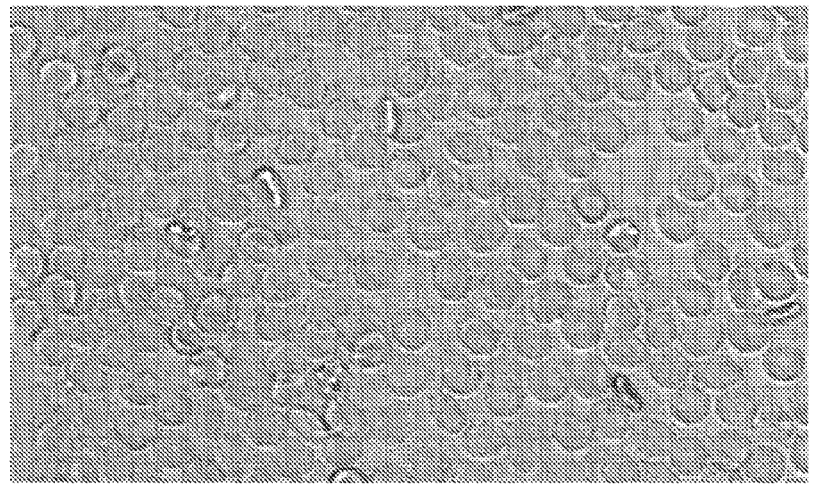
FIGS. 5A-5B show images of a blood sample obtained as a bright image of blood cells at 20× magnification with a monolayer coverage of 80% (FIG. 5A) and its corresponding florescent image (showing emissions at 460 nm) stained with Hoechst 33342 (FIG. 5B) In the image we show our ability to diagnose malaria causing *Plasmodium* trophozoites by distinguish between the malaria pathogen and platelets which are much smaller than RBC within the sample.
Figure 5B:
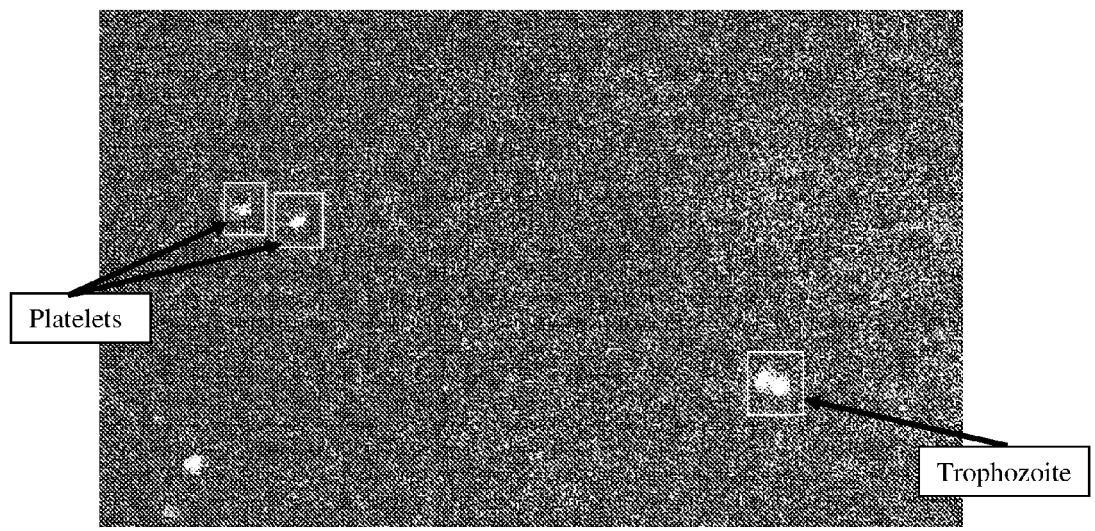

FIG. 5A is a brightfield image showing the spread, in the form of a continuous layer, of cells. FIG. 5B is a florescent image (emissions at 460 nm) showing the platelets and malaria infection (with two parasites in the same RBC, thus terms trophozoites). The florescent signal of the malaria parasite is stronger and distinguishable from that exhibited from the platelets, having similar size.

The invention claimed is:

1. A method comprising:
   introducing a cell suspension comprising red blood cells, into a carrier that includes a base surface;
   allowing the cells in the cell suspension to settle on the base surface of the carrier for a period of time that is at least 1 second per micrometer (μm) of a vertical height of the cell suspension when on the base surface, such as to form a monolayer of cells on the base surface of the carrier; and
   acquiring at least one microscope image of at least a portion of the monolayer of cells, the at least one microscope image being obtained by a microscope set to Depth Of Field (DOF) that is not more than 20% of the vertical height of the cell suspension when settled on the base surface.

2. The method of claim 1, wherein the vertical height of the cell suspension when settled on the base surface is between 20 μm and 1000 μm.

3. The method of claim 2, wherein the at least one microscope image is obtained by a microscope set to a DOF that is between 0.5 μm and 10 μm.

4. The method of claim 1, wherein the at least one microscope image is obtained by a microscope set to a DOF that is not more than 15% of the vertical height of the cell suspension when settled on the base surface.

5. The method of claim 1, further comprising, prior to the introducing, diluting a blood sample comprising the cells by a dilution factor (D) to obtain the cell suspension.

6. The method of claim 5, wherein the dilution factor (D) is between 50 and 300.

7. The method of claim 1, further comprising forming the cell suspension by diluting a blood sample comprising red blood cells to obtain a cell concentration such that, after the cell suspension settles on the base surface, the density of the cells of the cell suspension is between about 10,000 and about 30,000 cells per $mm^2$.

8. The method of claim 7, wherein forming the cell suspension comprises forming the cell suspension such that, after the cell suspension settles on the base surface, the cell suspension forms a monolayer having an average base surface coverage of between 40 percent and 90 percent.

9. The method of claim 1, further comprising selecting a microscope objective lens that provides the DOF, wherein the lens permits acquiring an image of at least one object being no more than 3 μm long at any dimension thereof.

10. The method of claim 9, wherein selecting the microscope objective lens comprises selecting a lens that permits acquiring an image of at least one object having a height with respect to the base surface of no more than 3 μm.

11. The method of claim 1, further comprising analyzing the at least one image to determine based thereon presence or absence of a pathogen in the cell suspension.

12. The method of claim 11, wherein analyzing the at least one image to determine based thereon presence or absence of a pathogen in the cell suspension comprises analyzing the at least one image to determine based thereon presence or absence of a blood infecting protozoa in the cell suspension.

13. The method of claim 12, wherein the blood infecting protozoa is selected from the genus consisting of *Trypanosoma, Plasmodium; Toxoplasma* and *Babesia*, and wherein analyzing the at least one image to determine based thereon presence or absence of the pathogen in the cell suspension comprises analyzing the at least one image to determine based thereon presence or absence of the blood infecting protozoa from the selected genus in the cell suspension.

14. The method of claim 1, wherein allowing the cells in the cell suspension to settle on the base surface of the carrier to form the monolayer of cells on the base surface of the carrier comprises allowing a period of time of less than 5 minutes for the cells to settle as a monolayer on the base surface.

15. The method of claim 1, wherein a vertical height of the carrier is between 20 μm and 300 μm.

16. The method of claim 1, wherein acquiring the at least one microscope image comprises acquiring a plurality of microscope images, at least two of which are provided under different conditions, the different conditions being selected from the group consisting of: different portions of the base surface being imaged, and different illumination conditions being used.

17. The method according to claim 1, wherein introducing the cell suspension into the carrier comprises introducing the cell suspension into the carrier, the cell suspension having a concentration that is such that when substantially all of the cells in the cell suspension are allowed to settle on the base surface of the carrier to form the monolayer of cells, a monolayer is formed on the surface with substantially no overlap between the cells.

18. A method for imaging a blood sample, the method comprising:
   introducing a cell suspension, onto a base surface of a carrier, wherein the cells are human cells comprising at least 75% red blood cells and at least a portion of the cells are suspected of being infected with a plasmodium parasite selected from the group consisting of *Plasmodium falciparum* (*P. falciparum*), *Plasmodium vivax* (*P. vivax*), *Plasmodium ovale* (*P. ovale*), *Plasmodium malariae* (*P. malariae*), and *Plasmodium knowlesi* (*P. knowlesi*);
   mixing the cells with one or more stains, the one or more stains including at least one fluorescent stain;
   allowing the cells in the cell suspension to settle on the base surface of the carrier, such as to form a monolayer of cells on the base surface of the carrier; and
   acquiring at least one microscope image of at least a portion of the monolayer of cells, the at least one microscope image being obtained by a microscope set to Depth Of Field (DOF) that is not more than 20% of a vertical height of the cell suspension when settled on the base surface, the acquiring of the at least one microscope image comprising acquiring a fluorescent image that is configured to facilitate detecting staining with the fluorescent stain.

19. A system for imaging a blood sample, the blood sample including human cells that include at least 75% red blood cells, at least a portion of the cells being suspected of being infected with a plasmodium parasite selected from the group consisting of *Plasmodium falciparum* (*P. falciparum*), *Plasmodium vivax* (*P. vivax*), *Plasmodium ovale* (*P. ovale*), *Plasmodium malariae* (*P. malariae*), and *Plasmodium knowlesi* (*P.knowlesi*), the blood sample including a blood cell diluting agent, the system comprising:
- one or more stains configured to be mixed with the blood sample, the one or more stains comprising at least one fluorescent stain;
- a blood sample preparing unit configured:
  - to receive the blood sample, and
  - to facilitate forming therefrom a blood cell suspension, that is such that the cell suspension forms a monolayer of the cells when allowed to settle on a base surface of a carrier;
- a microscope image acquisition unit configured to acquire at least one image of the blood cell suspension when on the base surface of the carrier, the at least one image including at least one fluorescent image that is configured to facilitate detecting of staining the fluorescent stain;
- a controller configured to drive the microscope image acquisition unit to acquire the at least one microscope image of the cell suspension using a microscope set to a Depth Of Field (DOF) that is not more than 20% of a vertical height of the cell suspension when settled on the base surface.

20. The system of claim 19, wherein the controller is configured to drive the microscope image acquisition unit to acquire a plurality of microscope images of the monolayer, at least two of which are provided under different conditions, the different conditions being selected from the group consisting of: different portions of the monolayer being imaged, and different illumination conditions being used.

21. The system according to claim 19, wherein the blood sample preparing unit is configured to facilitate forming a blood cell suspension, that is such that that when substantially all of the cells in the cell suspension are allowed to settle on the base surface of the carrier to form the monolayer of cells, a monolayer is formed on the base surface with substantially no overlap between the cells.

22. A system for imaging a blood sample comprising red blood cells and at least one blood cell diluting agent, the system comprising:
- a blood sample preparing unit comprising a carrier having a base surface, the blood sample preparing unit being configured:
  - to receive the blood sample, and
  - to facilitate forming therefrom a blood cell suspension, that is such that the cell suspension forms a monolayer of the cells when allowed to settle on the base surface of the carrier, by allowing the cells in the cell suspension to settle on the base surface of the carrier for a period of time that is at least 1 second per micrometer (μm) of a vertical height of the cell suspension when on the base surface;
- a microscope image acquisition unit configured to acquire at least one image of the blood cell suspension when on the base surface of the carrier;
- a controller being configured to drive the microscope image acquisition unit to acquire at least one microscope image of the cell suspension by a microscope set to a Depth Of Field (DOF) that is not more than 20% of a vertical height of the cell suspension when settled on the base surface.

* * * * *